(12) United States Patent
Tsai (10) Patent No.: US 9,295,694 B2
(45) Date of Patent: Mar. 29, 2016

(54) COMPOSITION COMPRISING SILVER NANOPARTICLES AND EXTRACTS OF POLYGONUM MULTIFORUM THUNB AND THE USE THEREOF

(75) Inventor: Mingfen Tsai, Taiwan (CN)

(73) Assignee: Skylight Technology Limited, Hong Kong (CN)

( * ) Notice: Subject to any disclaimer, the term of this patent is extended or adjusted under 35 U.S.C. 154(b) by 73 days.

(21) Appl. No.: 13/148,468

(22) PCT Filed: Feb. 10, 2009

(86) PCT No.: PCT/CN2009/000141
§ 371 (c)(1),
(2), (4) Date: Nov. 4, 2011

(87) PCT Pub. No.: WO2010/091529
PCT Pub. Date: Aug. 19, 2010

(65) Prior Publication Data
US 2012/0045480 A1    Feb. 23, 2012

(51) Int. Cl.
| | | |
|---|---|---|
| *A61K 33/38* | (2006.01) | |
| *A61K 9/14* | (2006.01) | |
| *A61K 8/02* | (2006.01) | |
| *A61K 8/11* | (2006.01) | |
| *A61K 8/19* | (2006.01) | |
| *A61K 8/64* | (2006.01) | |
| *A61K 8/81* | (2006.01) | |
| *A61K 8/97* | (2006.01) | |
| *A61K 36/704* | (2006.01) | |
| *A61Q 7/00* | (2006.01) | |

(52) U.S. Cl.
CPC ............ *A61K 33/38* (2013.01); *A61K 8/0241* (2013.01); *A61K 8/11* (2013.01); *A61K 8/19* (2013.01); *A61K 8/64* (2013.01); *A61K 8/8176* (2013.01); *A61K 8/97* (2013.01); *A61K 36/704* (2013.01); *A61Q 7/00* (2013.01); *A61K 2800/412* (2013.01); *A61K 2800/624* (2013.01)

(58) Field of Classification Search
CPC ....... A61K 36/00; A61K 36/26; A61K 36/73; A61K 33/38; A61K 9/14
See application file for complete search history.

(56) References Cited

U.S. PATENT DOCUMENTS

| 5,306,434 | A | * | 4/1994 | Schueller et al. ........... 424/70.12 |
| 7,927,631 | B2 | * | 4/2011 | Phillips ......................... 424/725 |

FOREIGN PATENT DOCUMENTS

| KR | 2007081211 | * | 8/2007 | |
| KR | 20080035848 | A | 4/2008 | |
| WO | WO-2007014497 | A1 | 2/2007 | |
| WO | WO 2007014497 | A1 * | 2/2007 | ............. A61K 33/38 |
| WO | WO 2007046636 | A1 * | 4/2007 | ............... A61K 8/97 |

OTHER PUBLICATIONS

PCT/ISA/210, WO, Nov. 19, 2009, ISR for PCT/CN2009/000141.
Japanese Office Action for JP Appln. No. 2009-191455 dated Dec. 10, 2013.

* cited by examiner

*Primary Examiner* — Michael G Hartley
*Assistant Examiner* — Jagadishwar Samala
(74) *Attorney, Agent, or Firm* — Bryan D. Zerhusen; Locke Lord LLP

(57) ABSTRACT

The present invention relates to a pharmaceutical composition comprising an effective amount of silver nanoparticles and extracts of *Polygonum Multiflorum* Thunb, a method for increasing hair growth by administering the pharmaceutical composition locally to a host, and use thereof.

10 Claims, 11 Drawing Sheets

Figures for illustration

PS:☐ : dressing area

Fig. 5

PS: ☐ : dressing area

CD34(+) cells per hair follicle (cross section, 400X)

Fig. 11

COMPOSITION COMPRISING SILVER NANOPARTICLES AND EXTRACTS OF POLYGONUM MULTIFORUM THUNB AND THE USE THEREOF

This application is the U.S. national phase, pursuant to 35 U.S.C. §371, of PCT international application Ser. No. PCT/CN2009/000141, filed Feb. 10, 2009, designating the United States and published in English on Aug. 19, 2010 as publication WO 2010/091529 A1, the entire disclosure of which is incorporated herein by this reference.

FIELD OF THE INVENTION

The present invention relates to a pharmaceutical composition comprising an effective amount of silver nanoparticles and extracts of *Polygonum Multiflorum* Thunb, a method for increasing hair growth by administering said pharmaceutical composition locally to a host and use of the pharmaceutical composition in manufacture of a medicament for increasing hair growth in a host.

BACKGROUND OF THE INVENTION

Metal nanoparticles have been attracting increasing attention to the chemical society due to their important applications in a number of subject areas such as catalysis and nanoscale electronics (references: (a) El-Sayed, M. A. *Acc. Chem. Res.* 2004, 37, 326. (b) Ho, C.-M.; Yu, W.-Y.; Che, C.-M. *Angew. Chem. Int. Ed.* 2004, 43, 3303. (c) Lang, H.; May, R. A.; Iversen, B. L.; Chandler, B. D. *J. Am. Chem. Soc.* 2003, 125, 14832. (d) Lewis, L. N. *Chem. Rev.* 1993, 93, 2693). Recently, much effort has been devoted to develop biomedical applications of metal nanoparticles. While significant advance in biological labeling has been made (references: (a) Nicewarner-Pena, S. R.; Freeman, R. G.; Reiss, B. D.; He, L.; Pena, D. J.; Walton, I. D.; Cromer, R.; Keating, C. D.; Natan, M. J. *Science* 2001, 294, 137. (b) Elghanian, R.; Storhoff, J. J.; Mucic, R. C.; Letsinger, R. L.; Mirkin, C. A. *Science* 1997, 277, 1078), few therapeutic applications of metal nanoparticles have been reported in the literature. A notable example is the anti-microbial properties of silver nanoparticles, which has been used for wound healing (Wright, J. B.; Lam, K.; Hansen, D.; Burrell, R. E. *Am. J. Inf. Cont.* 1999, 27, 344).

Alopecia areata is a condition in which there is hair loss on the scalp and elsewhere on the body. It has been reported to be associated with autoimmunity by which the hair follicles become attached by self immune system, resulting in an arrest of the hair growth. Another observation is that high levels of a naturally occurring hormone called dihydroxytestosteron (DHT) are present in the scalp of men genetically disposed to male pattern hair loss, the growth phase of hair is shortened. Eventually, the hairs become so small as to be practically invisible. This can result in the classic male bald hairline if it is not stopped.

Alopecia areata usually starts with one or more small, round, smooth bald patches on the scalp and can progress to total scalp hair loss (alopecia totalis) or complete body hair loss (alopecia universalis). Epidemiology-wise, alopecia areata affects approximately 1.7 percent of the population all over the world, including more than 4.7 million people in the United States alone, and this condition/disease has a profound impact on one's self-image and self-confidence, thereby affecting the life quality, both at work and at school.

Alopecia areata can occur in males and females of all ages and races. Its onset most often begins in childhood/early adulthood and can be psychologically devastating. Although alopecia areata is not life-threatening, it is most certainly life-altering, and its sudden onset, recurrent episodes, and unpredictable course have a profound psychological impact on the lives of those disrupted by this disease.

CONTENTS OF THE INVENTION

Combinational use of PVP-coated silver nano-particles and *Polygonum Multiflorum* Thunb has a synergistic effect in promoting hair growth. A pharmaceutical composition comprising an effective amount of silver nanoparticles and extracts of *Polygonum Multiflorum* Thunb is more potent than silver nanoparticles alone in inducing hair growth.

Therefore, the present invention relates to a pharmaceutical composition comprising an effective amount of silver nanoparticles, at least one stabilizer, extracts of *Polygonum Multiflorum* Thunb, and at least one pharmaceutically acceptable diluent.

The stabilizer may be, for example, one or more proteins and/or peptides, preferably human serum albumin or transferrin, and more preferably human serum albumin (HSA). In one embodiment, the stabilizer is polyvinylpyrrolidone.

The extracts of *Polygonum Multiflorum* Thunb are preferably extracts of the roots of *Polygonum Multiflorum* Thunb, and more preferably ethanol extracts of the roots of *Polygonum Multiflorum* Thunb.

In one embodiment, the silver nanoparticles in the pharmaceutical composition are 1 to 100 nm in diameter.

In one embodiment, the concentration of the silver nanoparticles in the pharmaceutical composition is 10 μM to 10 mM, and preferably 10 μM to 1 mM.

In one embodiment, the concentration of the extracts of *Polygonum Multiflorum* Thunb in the pharmaceutical composition is 1 g/L to 1000 g/L, and preferably 1 g/L to 100 g/L.

In a preferred embodiment, the pharmaceutical composition of the present application comprises a diluent selected from the group consisting of water, ethanol, DMSO, acetonitrile, Hepes buffer, phosphate buffer, Tris buffer, citrate buffer, serum or any other kinds of physiologically relevant solvent or solution, and a mixture thereof.

The present invention also relates to a method for increasing hair growth comprising administering locally the pharmaceutical composition of the present invention to a host in need thereof. The host is preferably human.

The present invention also relates to use of a pharmaceutical composition described hereinbefore in manufacture of a medicament for increasing hair growth in a host.

The present invention also relates to use of a pharmaceutical composition comprising an effective amount of silver nanoparticles and extracts of *Polygonum Multiflorum* Thunb in manufacture of a medicament for increasing hair growth in a host.

In the use of the present invention, the pharmaceutical composition comprises an effective amount of silver nanoparticles, extracts of *Polygonum Multiflorum* Thunb, at least one stabilizer and at least one pharmaceutically acceptable diluent.

In the use of the present invention, the stabilizer may be, for example, one or more proteins and/or peptides, preferably human serum albumin or transferrin, and more preferably human serum albumin (HSA). In one embodiment, the stabilizer is polyvinylpyrrolidone.

In the use of the present invention, the extracts of *Polygonum Multiflorum* Thunb are preferably extracts of the roots of *Polygonum Multiflorum* Thunb, and more preferably ethanol extracts of the roots of *Polygonum Multiflorum* Thunb.

In one embodiment of the use of the present invention, the silver nanoparticles in the pharmaceutical composition are 1 to 100 nm in diameter.

In one embodiment of the use of the present invention, the concentration of the silver nanoparticles in the pharmaceutical composition is 10 μM to 10 mM, and preferably 10 μM to 1 mM.

In one embodiment of the use of the present invention, the concentration of the extracts of *Polygonum Multiflorum* Thunb in the pharmaceutical composition is 1 g/L to 1000 g/L, and preferably 1 g/L to 100 g/L.

In a preferred embodiment of the use of the present invention, the pharmaceutical composition of the present application comprises a diluent selected from the group consisting of water, ethanol, DMSO, acetonitrile, Hepes buffer, phosphate buffer, Tris buffer, citrate buffer, serum or any other kinds of physiologically relevant solvent or solution, and a mixture thereof.

The host is preferably human.

There are numerous methods for generating silver nanoparticles with different shapes and sizes (references: (a) Raveendran, P.; Fu, J.; Wallen, S. L. *J. Am. Chem. Soc.* 2003, 125, 13940. (b) Sun, Y.; Xia, Y. *Science* 2002, 298, 2176. (c) Esumi, K.; Suzuki, A.; Yamahira, A.; Torigoe, K. *Langmuir* 2000, 16, 2604).

Human serum albumin (HSA) is the most abundant plasma protein in circulatory system. Previous reports showed that this serum protein could be used to stabilize a variety of metal nanoparticles (reference: Xie, H.; Tkachenko, A. G.; Glomm, W. R.; Ryan, J. A.; Brennaman, M. K.; Papanikolas, J. M.; Franzen, S.; Feldheim, D. L. *Anal. Chem.* 2003, 75, 5797).

The pharmaceutical composition of the invention comprising PVP-coated silver nano-particles and *Polygonum Multiflorum* Thunb has a synergistic effect in promoting hair growth.

MODE OF CARRYING OUT THE INVENTION

The present invention will now be further explained in the following examples. However, the present invention should not be construed as limited thereby. One of ordinary skill in the art will understand how to vary the exemplified preparations to obtain the desired results.

Examples

Materials and Methods

Materials.

All chemicals, except otherwise noted, were purchased from Sigma-Aldrich Chemical Co.

Cleaning the Glassware for Preparing Silver Nano-Particles

The conical flask was soaked in the base bath (200 g sodium hydroxide pellets in 2 L double distilled water (ddH2O)). The flask was washed with ddH2O, then with MilliQ water, and finally by concentrated nitric acid. A mixture of concentrated hydrochloric acid and concentrated nitric acid (volume ratio=1:3) was boiled in the conical flask for 30 minutes in order to remove all the metals in the flask. The conical flask was then washed with MilliQ water before the synthesis of silver nano-particles.

Preparation of Human Serum Albumin (HSA)-Coated Silver Nano-Particles 180 mg/L sodium citrate tri-basic dehydrate and 16 mg/L silver nitrate were added in 1 L MilliQ water and mixed for about 5 minutes. Then 50 mg sodium borohydride powder was added to the mixture and mixed for 20 minutes. A yellow solution was then observed and 12 g HSA was added to the solution.

After all the human serum albumin (HSA) was dissolved, the solution was filtered through a 22 μm filter top. The solution was stored in 4° C. before use Preparation of Polyvinylpyrrolidone (PVP)-Coated Silver Nano-Particles For preparing 100 ml of polyvinylpyrrolidone (PVP)-coated silver nano-particles, 5 g PVP-K30 (from Sigma-Aldrich Ltd, USA) was dissolved in 100 ml 60% ethanol, which after complete dissolution was subsequently added with 100 mg silver nitrate powder. 25 mg $NaBH_4$ in 1 ml of MilliQ water was then added to the solution. The final solution containing 0.1 mM of silver nano-particles was stored in 4° C. before use.

Topical Delivery of Tested Chemicals to Nude Mice

Four week old male athymic nude mice with Balb/c background were purchased from the Jackson Laboratory, USA. The animals were randomly divided into different groups to receive different treatments of daily dressing on a 1 cm×1 cm area on the back (collar or anterior saddle area) of the trunk for 8 weeks. The 1 cm×1 cm gauze was soaked with silver nano-particle solution (either coated with HSA or PVP) and was further covered with another 4 cm-width non-stretched cotton crepe bandage, followed by a 4 cm-width stretched bandage. The dressing was finally fixed with adhesive tapes. After 8 week's treatment, the mice were sacrificed by cervical dislocation, and skin pieces from the dressed areas were harvested and fixed with 4% paraformaldehyde for analysis.

Preparation of *Polygonum Multiflorum* Thunb (PMT)

Figure 1:
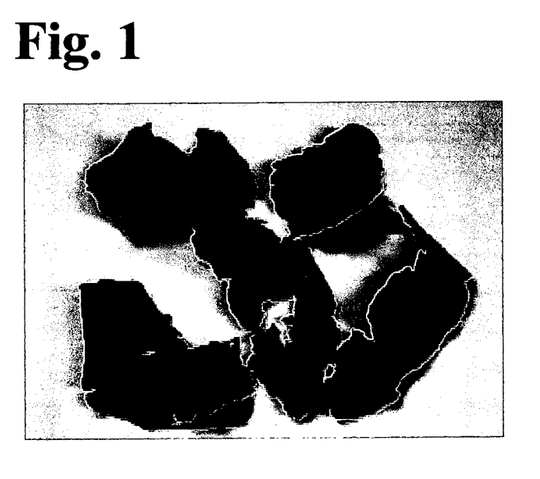
FIG. 1 is the photo of *Polygonum multiflorum* Thunb.

Three types of samples were prepared and isolated from the ethanol extract of the roots of *Polygonum Multiflorum* Thunb; they are:

(A) Root Extracts (See FIG. 1)

100 g of the dried roots of PM were mashed and immersed in 1000 ml of 50% ethanol (i.e., ratio of "roots vs. 50% ethanol" was "1:10"). After 48 hours, the solution was collected and filtered off, and was subsequently concentrated under reduced pressure with a vacuum rotary evaporator. The concentrated extracts were subsequently frozen and dried, and stored at 4° C. until use. An amount of 10 g of dried extracts is usually obtained from 100 g of the dried roots of PMT. For experiments, 100 g of the dried extracts powder was dissolved in 1000 ml (i.e., 10% of w/v) $ddH_2O$ at 70° C., and after complete dissolution, PMT solution was stored at 4° C. until use.

(B) Dissolution of Commercially Available PMT Tablets

Figure 2:
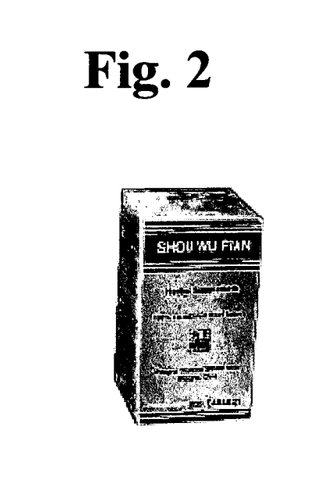
FIG. 2 is the photo of PMT tablets commercially available from Shou Wu Pian, Shanghai Lei Yun Shang Pharmaceutical Co. Ltd.

*Polygonum Multiflorum* Thunb (PMT) solution used in this study was also prepared by dissolving 100 g PMT tablets (commercially available from Shou Wu Pian, Shanghai Lei Yun Shang Pharmaceutical Co. Ltd, China-see FIG. 2) in 1000 ml $ddH_2O$ at 70° C., and after complete dissolution, PMT solution was stored at 4° C. until use.

Mixture of PMT with PVP-Coated Silver Nano-Particles

To make mixture of PVP-coated silver nano-particles with PMT, the PVP-coated silver nano-particle solution is prepared as described above except PVP is dissolved in absolute ethanol instead of 60% ethanol. 100 g/L dissolved PMT solution was mixed with 0.17 mM PVP-coated silver nano-particle solution in a volume ratio of 4:6.

Calculation of the Hair Coverage Area at the Treated Skin

Figure 3:
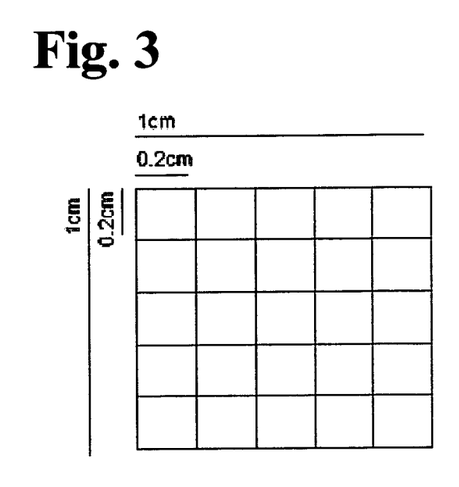
FIG. 3 shows a 1 cm×1 cm transparent film with 0.2 cm×0.2 cm square grid.

The hair coverage area is measured by placing a 1 cm×1 cm transparent film (with 0.2 cm×0.2 cm square grid, as shown in FIG. 3) above the skin.

The percentage of hair covered is calculated in mice with visible new hair growth after treatment by the following equation:

$$\frac{\text{Number of squares covered with hair}}{25} \times 100\%$$

In Situ Hybridization (ISH) for CD34 and Immunostaining for Ki67

In situ hybridization for mouse CD34 was performed in 5 μm thick paraffin-fixed sections formalin-fixed tissues. Paraffin-fixed slides were dewaxed with xylene and then rehydrated with graded concentration of ethanol. After dewaxing, sections were incubated in a solution containing 0.2N HCl and 0.3% Triton in room temperature for 30 minutes, and then digested with 10 μg/ml proteinase-K (Invitrogen) at 37° C. for 15 minutes. The PK digestion was stopped by 0.1M glycine for 10 minutes at room temperature. The sections were washed in 2×SSC and hybridized with 2 ng/μl DIG-labeled sense and antisense cRNA probe overnight at 46° C. in a hybridization buffer containing 50% deionized formamide, 2×SSC, 10% Dextran sulphate, 5×Denhardt's Solution, 0.25 mg/ml yeast tRNA, 0.5% SDS. Sections were washed in 2×SSC/50% formamide at 46° C. for 15 minutes twice, then in 0.1×SSC/30% formamide at 46° C. for 15 minutes, then in 0.1×SSC/30% formamide in room temperature for 15 minutes, and in 0.1×SSC in room temperature for 15 minutes. The hybridized probes were detected using alkaline phosphatase-conjugated sheep anti-DIG F(ab) fragments (Roche) and color development with NBT/BCIP solution (Roche). Sections were then mounted with medium for fluorescence with DAPI (Vector Laboratories). The DIG-labelled mouse CD34 probe corresponds to nucleotides 379-773 [NM_133654 (mus musculus CD34 antigen (CD34), mRNA)].

The staining for Ki67 was performed in 5 μm thick paraffin-fixed sections of formalin-fixed skin tissue. Paraffin-fixed slides was dewaxed with xylene and then rehydrated with graded concentration of ethanol. The sections were subsequently heated in 10 mM sodium citrate buffer (pH 6.0) for 15 minutes in a microwave. The slides were then stained with 1:200 rabbit anti-Ki67 antibody (LabVision, United States) or with the same concentration of purified rabbit IgG (Zymed, USA; as an isotype) at 4° C. for overnight. After that, the sections were incubated with 1:200 AlexaFluor 594 goat anti-rabbit IgG (H+L) antibody (Molecular Probes, USA) at room temperature for 1 hour. The sections were finally mounted with VECTASHIELD® with DAPI (Vector Laboratories, United States). The image was studied under fluorescence microscope (Nikon E600 microscope).

In parallel to the experiment, positive and negative controls were included. The positive controls were mouse spleen sections. The negative controls were skin sections stained with purified rabbit IgG as the primary antibody.

Nuclear staining of Ki-67 was considered positive. The percentage of Ki67-positive cells was calculated by $$\% \text{ of } Ki67\text{-positive cells} = \frac{\text{No. of } Ki\text{-}67 \text{ positive cells}}{\text{No. of } DAPI \text{ positive cells}}$$

Body Weight Measurement of the Tested Animals

The body weights of mice were measured by an electric balance twice a week.

Results

1. Transcutaneous (topical) application of 0.1 mM silver nano-particles (nanoAg) coated with PVP (nanoAg-PVP) induced hair growth in nude mice whereas mixture of nanoAg-PVP with and 5% minoxidil reduced such an effect.

Figure 4:
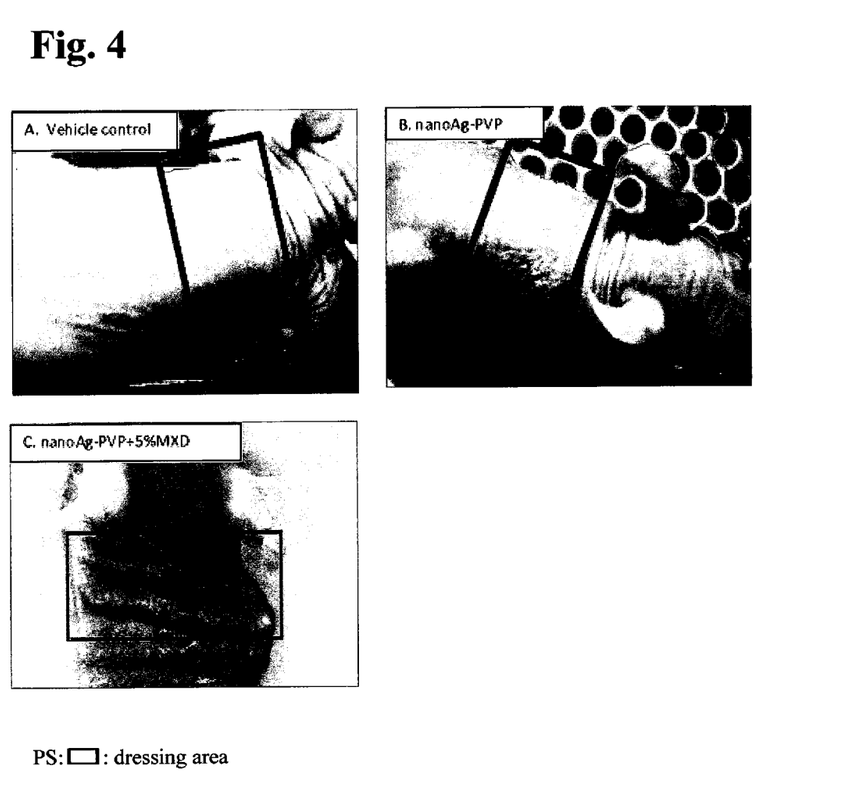
FIG. 4 are the photos at the anterior saddle region of mice after treatment for 8 weeks with vehicle control (PVP only. panel A), silver nanoparticles coated with PVP (nanoAg-PVP, panel B) or PVP-coated silver nanoparticles mixed with 5% minoxidil, panel C). NanoAg-PVP appears to induce new hair growth whereas addition of 5% minoxidil reduces this effect.

FIG. 4 are the photos at the anterior saddle region of mice after treatment for 8 weeks with vehicle control (PVP only, panel A), silver nanoparticles coated with PVP (nanoAg-PVP, panel B) or PVP-coated silver nanoparticles mixed with 5% minoxidil, panel C). NanoAg-PVP appears to induce new hair growth whereas addition of 5% minoxidil reduces this effect.

TABLE 1.1

Percentage of skin surface area covered by hair in the dressing area after treatment for 8 weeks with vehicle control, 0.1 mM nanoAg-PVP, or 0.1 mM nanoAg-PVP mixed with 5% minoxidil. The addition of 5% minoxidil appears to reduce the hair-growing effect of nanoAg-PVP ($p < 0.001$ by t-test).

| | Conditions | | |
|---|---|---|---|
| Parameters (day 56) | Vehicle control (PVP alone) | nanoAg-PVP | nanoAg-PVP + 5% Minoxidil (MXD) |
| No. of mice with visible hair growth | 0/16 (0%) | 13/16 (81.3%) | 8/16 (50%) |
| % of hair coverage in dressing area (mean ± SD) | 0% | 72 ± 8% | 28 ± 11%* |

PS:
*$p < 0.001$, compared with nanoAg-PVP

2. Mixture of nanoAg-PVP plus 10% PMT is more potent than nanoAg-PVP alone in inducing hair growth, whereas 10% PMT alone had no effect.

Figure 5:
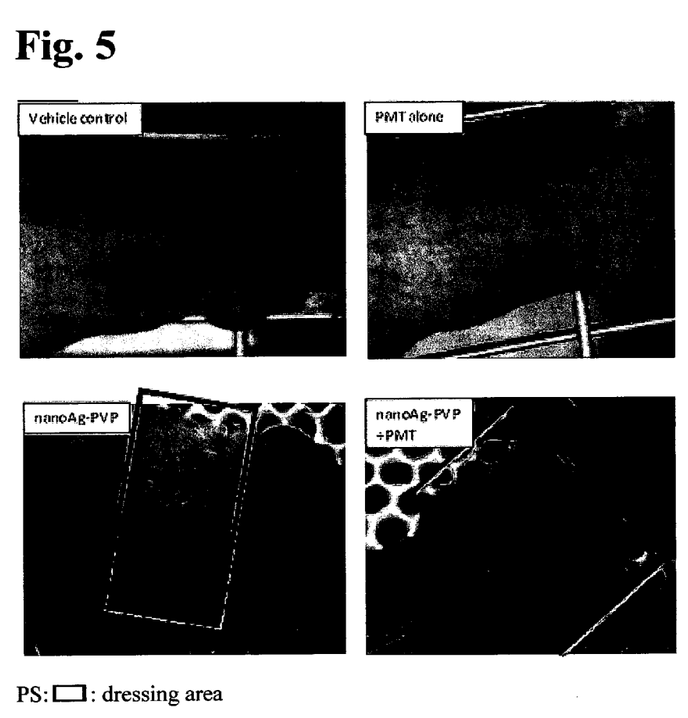
FIG. 5 are the photos of mice after treatment for 8 weeks with vehicle control (PVP alone), 10% PMT alone, 0.1 mM PVP-coated silver nanoparticles (nanoAg-PVP) or the mixture of 0.1 mM nanoAg-PVP and 10% PMT.

As seen from FIG. 5, addition of PMT synergizes the hair-growing effect of 0.1 mM nanoAg-PVP. Mice were treated for 8 weeks with vehicle control (PVP alone), 10% PMT alone, 0.1 mM PVP-coated silver nanoparticles (nanoAg-PVP) or the mixture of 0.1 mM nanoAg-PVP and 10% PMT. Mice treated with nanoAg-PVP+PMT had significantly more hair coverage area than those treated with nanoAg-PVP (panel at right lower vs left lower).

TABLE 2.1

The response rate and the percentage of hair covered area in the dressed area of the skin in nude mice treated with PVP alone (vehicle control), 10% PMT, 0.1 mM nanoAg-PVP, or 0.1 mM nanoAg-PVP plus 10% PMT for 8 weeks. The response rate in each group was 0%, 0%, 75% and 91.7% respectively. In those with hair growth, the percentage of hair coverage area in the dressed skin was 74.5 ± 7.4% for the mice treated with 0.1 mM nanoAg-PVP, and 88.9 ± 8.8% for those treated with nanoAg-PVP plus 10% PMT.

| | Conditions | | | |
|---|---|---|---|---|
| Parameters | PVP alone | 10% PMT alone | nanoAg-PVP | nanoAg-PVP + 10 PMT % |
| No. of mice with visible hair growth | 0/6 (0%) | 0/6 (0%) | 10/12 (83.3%) | 11/12 (91.7%) |
| % of hair coverage area | 0% | 0% | 74.5 ± 7.4% | 88.9 ± 8.8% |

Figure 6:
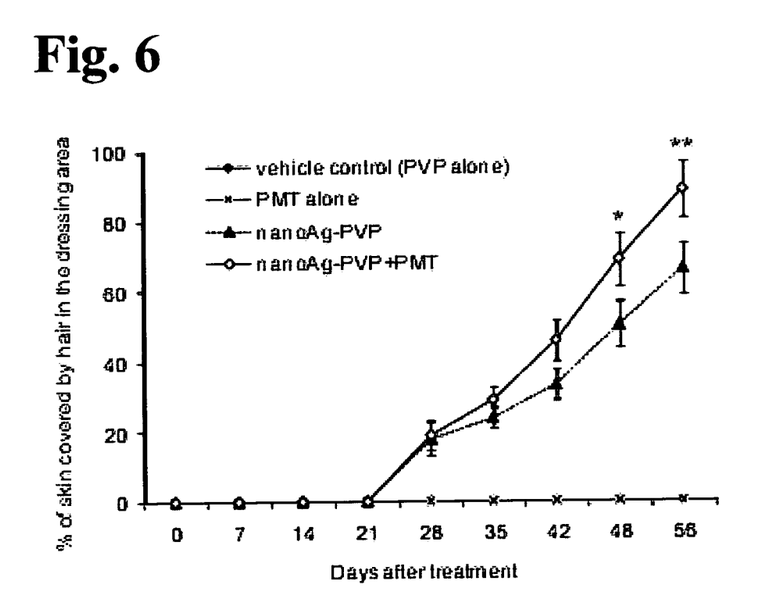
FIG. 6 shows the percentage of hair coverage area in the dressed skin of mice treated with PVP alone (vehicle control), 10% PMT alone, 0.1 mM nanoAg-PVP, and 0.1 mM nanoAg-PVP plus 10% PMT at 3, 4, 5, 6, 7, and 8 weeks post-treatment.

As seen from FIG. 6, the percentage of hair coverage area in the dressed skin of mice treated with PVP alone (vehicle control), 10% PMT alone, 0.1 mM nanoAg-PVP, and 0.1 mM nanoAg-PVP plus 10% PMT at 3, 4, 5, 6, 7, and 8 weeks post-treatment. At 7 and 8 week after treatment, mice treated with nanoAg-PVP+PMT had significantly higher hair coverage area than those treated with nanoAg-PVP alone. The response rate and the actual percentage of hair coverage area at 8 weeks are also listed in Table 2.1. (*$p<0.05$; **$p<0.01$).

3. 10% (w/v) PMT has the most optimal synergistic effect of PMT when mixed with nanoAg-PVP solution for promoting hair growth

TABLE 3.1

In separate experiments, the response rate and the percentage of hair coverage area in the dressed skin of nude mice was measured after 8 week's treatment with solutions containing (1) nanoAg-PVP alone (2) nanoAg-PVP plus 1% (w/v) PMT, (3) nanoAg-PVP plus 10% PMT, and (4) nanoAg-PVP plus 50% PMT. Optimal effects of promoting hair growth was seen in nanoAg-PVP with addition of 10% or 50% PMT (please refer to FIG. 7)

| | conditions | | | |
|---|---|---|---|---|
| Parameters | nanoAg-PVP alone | nanoAg-PVP + 1% PMT | nanoAg-PVP + 10% PMT | nanoAg-PVP + 50% PMT |
| No. of mice with visible hair growth | 6/8 (75%) | 7/8 (87.5%) | 8/8 (100%) | 7/8 (87.5%) |
| % of hair coverage area | 69.3 ± 4% | 69.1 ± 6.1% | 87.3 ± 4.1%* | 84.8 ± 3.9%* |

Figure 7:
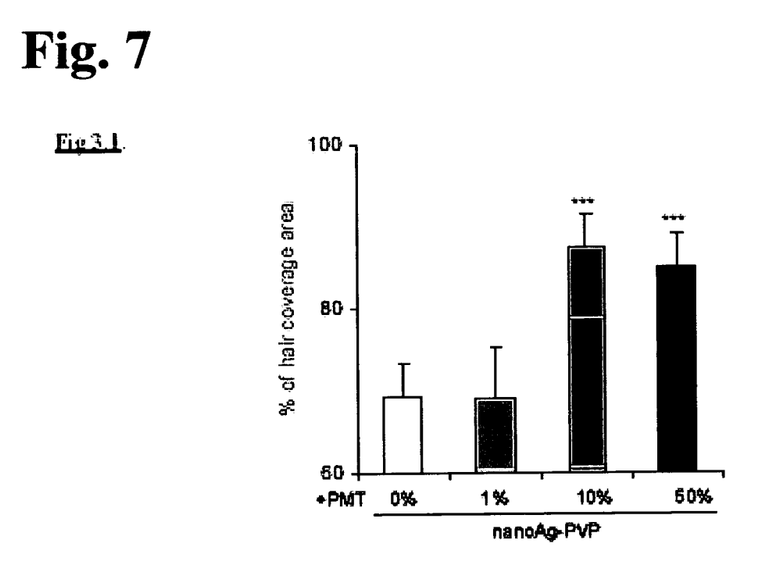
FIG. 7 shows the percentage of hair coverage area in the dressed skin of nude mice measured after 8 week's treatment with solutions containing (1) nanoAg-PVP alone (2) nanoAg-PVP plus 1% (w/v) PMT, (3) nanoAg-PVP plus 10% PMT, and (4) nanoAg-PVP plus 50% PMT (n=6, 7, 8, and 7 respectively, see Table 3.1).

As seen from FIG. 7, the percentage of hair coverage area in the dressed skin of nude mice was measured after 8 week's treatment with solutions containing (1) nanoAg-PVP alone (2) nanoAg-PVP plus 1% (w/v) PMT, (3) nanoAg-PVP plus 10% PMT, and (4) nanoAg-PVP plus 50% PMT (n=6, 7, 8, and 7 respectively, see Table 3.1). Optimal effects of promoting hair growth was seen in nanoAg-PVP with addition of 10% or 50 PMT. ***$p<0.001$ between the addition of 0% and 10%, and also between 0% and 50%. No statistical difference between the addition of 0% and 1%, or between 10% and 50%.

4. Both nanoAg-PVP and nanoAg-PVP+10% PMT induced the expression Ki67 and CD34 of the cells at the hair roots (compared with mice treated with vehicle alone), whereas a higher CD34+ cell number was seen in mice treated with nanoAg-PVP+10% PMT.

Figure 8:
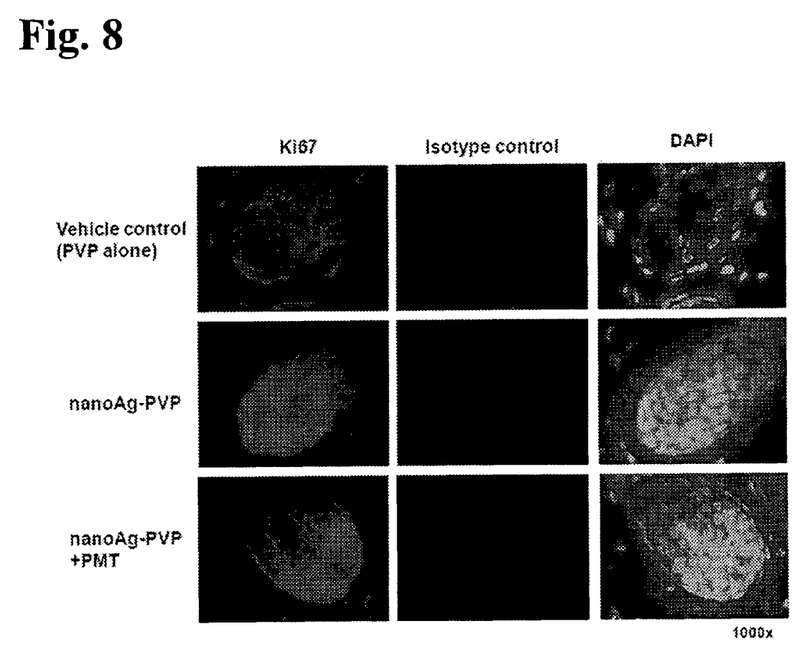
FIG. 8 shows Ki67 staining at the skin (cross section) of nude mice treated trans-cutaneously for 8 weeks with 0.1 mM nanoAg-PVP or 0.1 mM nanoAg-PVP+10% PMT.

FIG. 8 shows Ki67 staining at the skin (cross section) of nude mice treated trans-cutaneously for 8 weeks with 0.1 mM nanoAg-PVP or 0.1 mM nanoAg-PVP+10% PMT. Mice in both treated groups had increased Ki67 (+) cells at the hair roots (left column). Isotype controls were in the middle column, and DAPI showing cellular nuclei was in the right column. Results are representative of 3 independent experiments.

Figure 9:
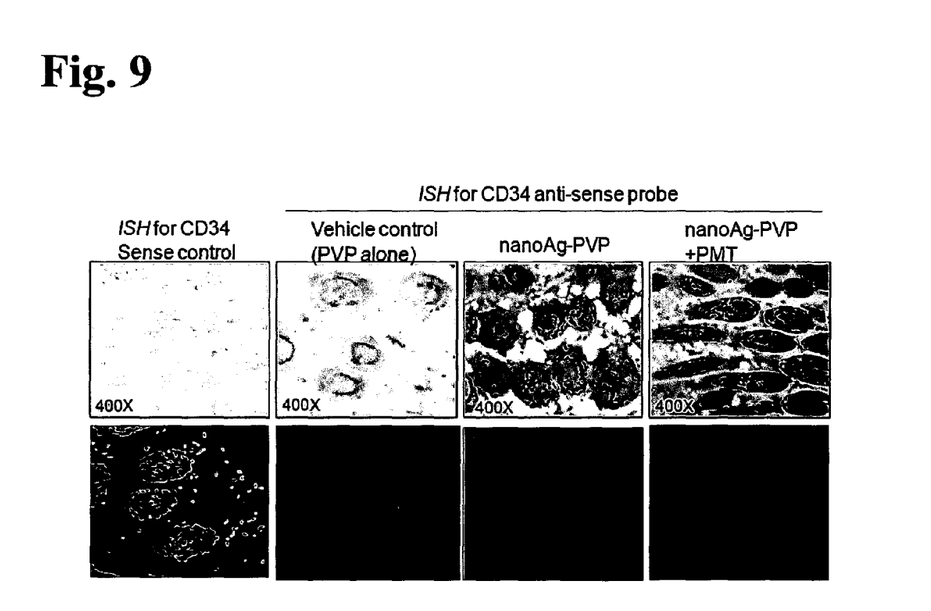
FIG. 9 shows in situ hybridization (ISH) for CD34 at the cross section (400×) of the skin treated with nanoAg-PVP or nanoAg-PVP+PMT.

FIG. 9 shows in situ hybridization (ISH) for CD34 at the cross section (400×) of the skin treated with nanoAg-PVP or nanoAg-PVP+PMT. Compared with the treatment by vehicle control (PVP alone), treatment with nanoAg-PVP and nanoAg-PVP+PMT induced more CD34 mRNA expression at the hair sheath, and more CD34+ cells were found in the group treated with nanoAg-PVP+PMT. The sense control for CD34 was shown in the left column. DAPI counterstaining to show the cellular nuclei was shown in the lower row. Results are representative of 3 independent experiments.

Figure 10:
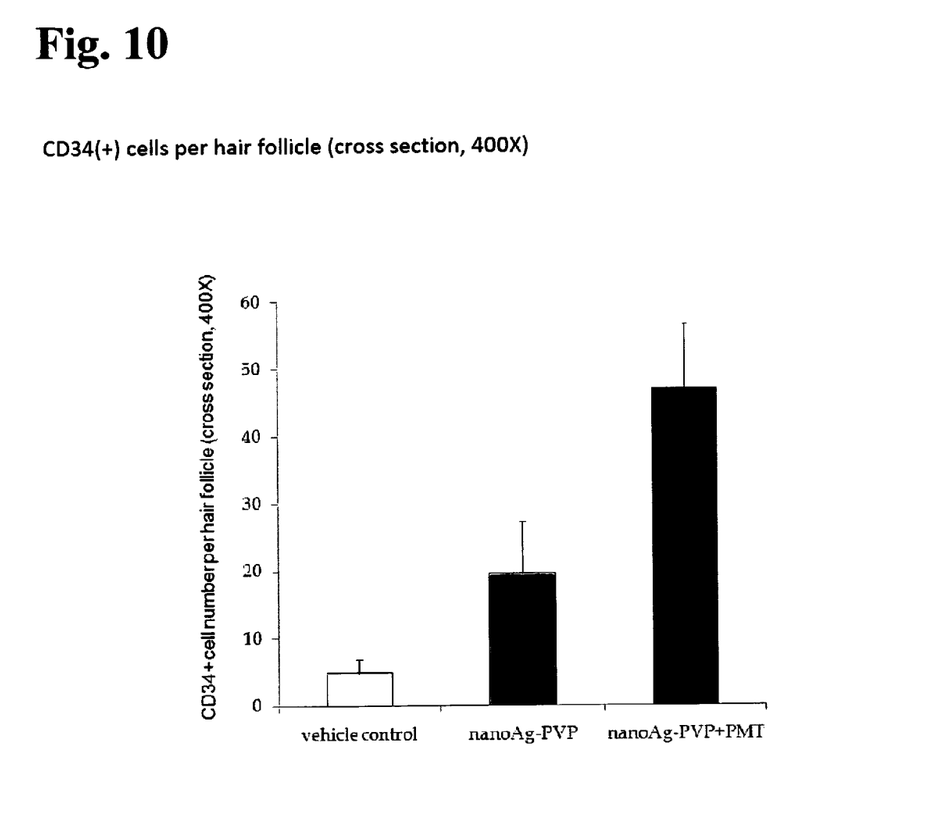
FIG. 10 shows numbers of the CD34+ cells (by ISH) per hair follicle (counted at cross section of hair sheath, 400×, similarly shown in FIG. 9) in the dressed skin of mice with different treatment.

FIG. 10 shows numbers of the CD34+ cells (by ISH) per hair follicle (counted at cross section of hair sheath, 400×, similarly shown in FIG. 9) in the dressed skin of mice with different treatment. Treatment with addition of 10% PMT in the nanoAg-PVP induced significantly more CD34+ cells than the treatment with nanoAg-PVP ($p<0.05$). Results are representative of 3 independent experiments.

Figure 11:
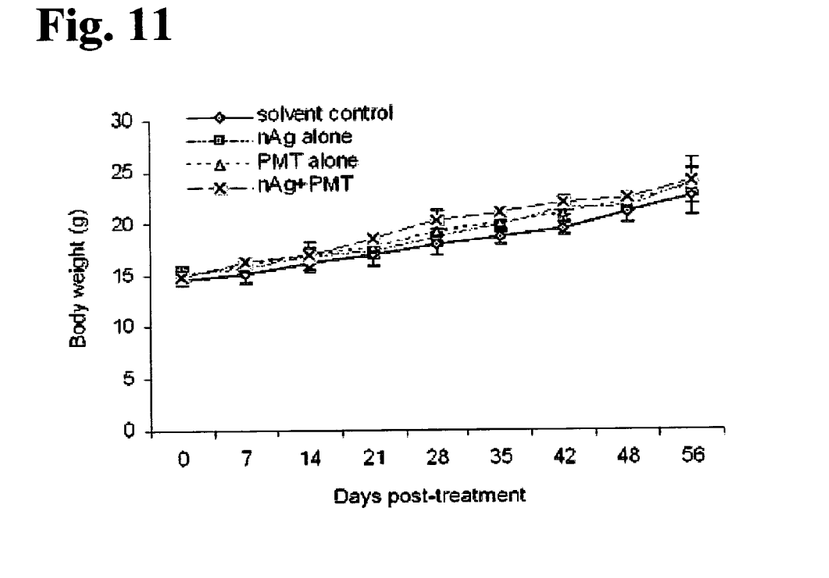
FIG. 11 shows measurement of body weight of mice treated with various conditions.

5. Topical application for 8 weeks did not cause noticeable changes in body weight gain FIG. 11 shows measurement of body weight of mice treated with various conditions. The body weight of mice under treatment was monitored every week, and there was no significant change of the body weight in mice among different groups along the course of treatment, indicating that none of the treatment caused significant or noticeable systemic effects on general conditions of the mice. Note: nAg=nanoAg; PMT used here was 10% (w/v).

What is claimed is:

1. A pharmaceutical composition comprising an effective amount of silver nanoparticles, at least one stabilizer, extracts of *Polygonum Multiflorum* Thunb, and at least one pharmaceutically acceptable diluent;
   wherein one of said stabilizers is polyvinylpyrrolidone; and
   the concentration of the extracts of *Polygonum Multiflorum* Thunb in the composition is 10% (w/v) to 40% (w/v).

2. The pharmaceutical composition of claim 1 wherein the extracts of *Polygonum Multiflorum* Thunb are extracts of the roots of *Polygonum Multiflorum* Thunb.

3. The pharmaceutical composition of claim 2 wherein the extracts of the roots of *Polygonum Multiflorum* Thunb are ethanol extracts of the roots of *Polygonum Multiflorum* Thunb.

4. The pharmaceutical composition of claim 1 wherein the silver nanoparticles are 1 to 100 nm in diameter and the concentration of the silver nanoparticles in the composition is 10 μM to 10 mM.

5. The pharmaceutical composition of claim 4 wherein the concentration of the silver nanoparticles in the composition is 10 μM to 1 mM.

6. The pharmaceutical composition of claim 1 wherein the diluent is selected from the group consisting of water, ethanol, DMSO, acetonitrile, Hepes buffer, phosphate buffer, Tris buffer, citrate buffer, serum or any other kinds of physiologically relevant solvent or solution, and a mixture thereof.

7. A method for increasing hair growth comprising administering locally the pharmaceutical composition according to claim 1 to a host in need thereof.

8. The method of claim 6 wherein the host is human.

9. A method of producing a pharmaceutical composition according to claim 1, said method comprising a step of mixing the silver nanoparticles and polyvinylpyrrolidone with the extracts of *Polygonum Multiflorum* Thunb, wherein the pharmaceutical composition is effective in increasing hair growth in a host.

10. The method of claim 9 wherein the host is human.

\* \* \* \* \*